US009595096B2

(12) United States Patent
Dorris et al.

(10) Patent No.: US 9,595,096 B2
(45) Date of Patent: Mar. 14, 2017

(54) COMPOSITE INSPECTION AND STRUCTURAL CHECK OF MULTIPLE LAYERS

(71) Applicant: The Boeing Company, Chicago, IL (US)

(72) Inventors: Steven A. Dorris, St. Peters, MO (US); Arun Ayyagari, Seattle, WA (US); Jonathan Blake Vance, University City, MO (US); David E. Corman, Creve Coeur, MO (US); James W. Fonda, Summerville, SC (US); Roger W. Engelbart, St. Louis, MO (US); Philip L. Freeman, Summerville, SC (US)

(73) Assignee: The Boeing Company, Chicago, IL (US)

( * ) Notice: Subject to any disclaimer, the term of this patent is extended or adjusted under 35 U.S.C. 154(b) by 450 days.

(21) Appl. No.: 14/202,376

(22) Filed: Mar. 10, 2014

(65) Prior Publication Data

US 2015/0254835 A1 Sep. 10, 2015

(51) Int. Cl.
*G06K 9/00* (2006.01)
*G06T 7/00* (2006.01)
(Continued)

(52) U.S. Cl.
CPC ....... *G06T 7/0006* (2013.01); *G01N 21/8422* (2013.01); *G01N 21/95* (2013.01);
(Continued)

(58) Field of Classification Search
CPC .. G06T 7/0006; G06T 7/0008; G01N 21/8422
See application file for complete search history.

(56) References Cited

U.S. PATENT DOCUMENTS 5,562,788 A 10/1996 Kitson et al.
6,264,869 B1 * 7/2001 Notarpietro ......... B29C 45/1671
264/247

(Continued)

FOREIGN PATENT DOCUMENTS

WO 2006093703 A1 9/2006
WO 2013156124 A1 10/2013

OTHER PUBLICATIONS

"Canadian Application Serial No. 2,883,726, Office Action mailed Mar. 17, 2016", 4 pgs.

(Continued)

*Primary Examiner* — Gregory M Desire
(74) *Attorney, Agent, or Firm* — Kwan & Olynick LLP

(57) ABSTRACT

Provided are methods, systems, and computer program products for inspecting composite items. Specifically, a method involves analyzing an image of or, more generally, data characterizing condition of a top layer, which is disposed over a bottom layer. The method also involves performing a structural integrity check based on any anomalies detected in the top layer during this analysis as well as based on any anomalies previously detected in the bottom layer. As such, this structural integrity check accounts for characteristics of multiple layers, in some embodiments, all layers applied up to point of this inspection. In addition to the detected anomalies, the structural integrity check may account for previously performed repairs. The structural integrity check may be performed on individual portions of a composite item while, for example, other portions continue receiving a new composite layer, which may be referred to as an inline inspection.

18 Claims, 6 Drawing Sheets

(51) Int. Cl.
*G01N 21/84* (2006.01)
*G01N 21/95* (2006.01)
*B29C 70/38* (2006.01)

(52) U.S. Cl.
CPC ............ *G06T 7/0008* (2013.01); *B29C 70/38* (2013.01); *G01N 2021/8438* (2013.01); *G01N 2021/8472* (2013.01); *G06T 2207/30124* (2013.01); *G06T 2207/30136* (2013.01)

(56) References Cited

U.S. PATENT DOCUMENTS

| | | | |
|---|---|---|---|
| 7,039,485 B2 | 5/2006 | Engelbart et al. | |
| 7,362,437 B2 | 4/2008 | Engelbart et al. | |
| 7,480,037 B2 | 1/2009 | Palmateer et al. | |
| 7,495,758 B2 | 2/2009 | Walton | |
| 7,555,404 B2 | 6/2009 | Brennan et al. | |
| 7,835,567 B2 | 11/2010 | Oldani | |
| 7,889,907 B2 | 2/2011 | Engelbart et al. | |
| 8,068,659 B2 | 11/2011 | Engelbart et al. | |
| 8,184,281 B2 | 5/2012 | Engelbart et al. | |
| 8,524,021 B2 | 9/2013 | Engelbart | |
| 2002/0031249 A1* | 3/2002 | Komuro | G01N 21/9501 382/149 |
| 2002/0142111 A1* | 10/2002 | Auld | B44C 3/02 428/13 |
| 2003/0148044 A1* | 8/2003 | Auld | B44C 3/02 428/13 |
| 2005/0004774 A1* | 1/2005 | Volk | G01N 21/9501 702/108 |
| 2005/0025350 A1 | 2/2005 | Engelbart et al. | |
| 2006/0142971 A1* | 6/2006 | Reich | G01C 17/00 702/150 |
| 2007/0156379 A1* | 7/2007 | Kulkarni | H01L 21/67005 703/14 |
| 2008/0167829 A1* | 7/2008 | Park | G01N 21/8851 702/81 |
| 2013/0301903 A1* | 11/2013 | Sohn | G06T 7/001 382/145 |
| 2015/0099422 A1 | 4/2015 | Deleris et al. | |
| 2015/0254835 A1* | 9/2015 | Dorris | G06T 7/0006 382/141 |

OTHER PUBLICATIONS

"European Application Serial No. 15158276.4, Search Report mailed Oct. 7, 2015", 6 pgs.

\* cited by examiner

COMPOSITE INSPECTION AND STRUCTURAL CHECK OF MULTIPLE LAYERS

TECHNICAL FIELD

The present disclosure generally relates to methods and systems for inspecting composite items. More particularly, the present disclosure relates to methods and systems for performing structural integrity checks based on any anomalies detected on currently inspected composite layers as well as based on anomalies previously detected on one or more layers disposed underneath the currently inspected composite layers.

BACKGROUND

Composite items are generally constructed from multiple layers that may be laminated together. These composite layers may be referred to as partial or full plies. For items having dimensions exceeding the available width of the material used to form the composite layers, each layer is typically formed from a series of strips or courses of the material. These strips or courses may be placed next to each other, such as in an edge to edge configuration or having some overlap. The material used for composite items may be woven fiber fabrics, unidirectional fiber materials (e.g., tapes), metal foils, adhesive films, and a variety of other conformations. The fibers may be made from natural and/or man-made materials, such as fiberglass, graphite, and the like.

The strips or courses are generally laid based a specific pattern or configuration to form each composite layers. Deviations from this pattern may result in wrinkles, twist, gaps, overlaps or, more generally height variations, which may be referred to as anomalies. Other types of anomalies include foreign objects, such as bits of backing material, debris, and blobs, which may appear on the surface of a composite layer as the layer is being formed. It is desirable for these anomalies to be identified and corrected prior to placement of the next layer.

Inspection of such composite layers for anomalies can be performed manually with human technicians or with conventional machine vision systems. Manual inspection may increase fabrication time and expense. Conventional machine vision systems may be implemented to increase the overall production rate and minimize human errors. Both of these inspection approaches typically inspect only one layer at a time and provide information about anomalies in currently inspected layer. Other layers disposed under the currently inspected layer may not be considered when determining a course of action.

SUMMARY

Provided are methods, systems, and computer program products for inspecting composite items. Specifically, a method involves analyzing an image of or, more generally, data characterizing condition of a top layer, which is disposed over a bottom layer. The method also involves performing a structural integrity check based on any anomalies detected in the top layer during this analysis as well as based on any anomalies previously detected in the bottom layer. For example, a 3D anomaly map may be used for performing structural integrity check. The 3D map may include all anomalies previously detected for this fabricated composite item or, more specifically, any detected anomalies on the portion of the top composite layer and any anomalies previously detected on an underlying portion of the at least one bottom composite layer. The 3D map may be constructed using multiple images for different layer. As such, the 3D map will include information about location of each anomaly within a layer and which layer this anomaly is in. Overall, this structural integrity check accounts for characteristics of multiple layers, in some embodiments, all layers applied up to point of this inspection. In addition to the detected anomalies, the structural integrity check may account for previously performed repairs. The structural integrity check may be performed on individual portions of a composite item while, for example, other portions continue receiving a new composite layer, which may be referred to as an inline inspection.

In some embodiments, a method of inspecting a composite item involves receiving an image of a portion of a top composite layer. The image may contain various information characterizing conditions of this portion. For example, the received image may include surface height variations of the top composite layer in this portion. The top composite layer may be disposed over at least one other composite layer, which may be referred to as a bottom composite layer. The method may involve analyzing the image to detect anomalies on the portion of the top composite layer. The method may also involve performing a structural integrity check based on any detected anomalies on the portion of the top composite layer as well as based on any anomalies previously detected on the underlying portion of the at least bottom composite layer. As noted above, any detected anomalies on the portion of the top composite layer as well as based on any anomalies previously detected on the underlying portion of the at least bottom composite layer may be presented in a 3D anomaly map. In some embodiments, analyzing the image to detect anomalies on the portion of the top composite layer also involves updating the 3D anomaly map.

In some embodiments, performing the structural integrity check may be also based on any repairs performed on the underlying portion of the at least one bottom composite layer or, more specifically, all bottom composite layers. For example, during a previous inspection round, it could have been determined that at least one of the underlying composite layers needed one or more repairs. This information may be included in a 3D anomaly map. These repairs may in the underlying portion that is now disposed below the inspected portion of the top composite layer. This repair may be considered while performing the structural integrity check of the top composite layer since this repair may impact the structural integrity of the composite item in that area. Furthermore, this repair may be taken into account to determine any new repairs that may be need to perform on the top composite layer. Again, this information may be included in a 3D anomaly map. In some embodiments, performing the structural integrity check involves identifying severity of the detected anomaly.

Performing the structural integrity check may be also based on any detected anomalies on corresponding portions of one or more previously fabricated composite items. Specifically, two or more 3D anomaly maps may be compared. In other words, the structural integrity check may take into account part-to-part variations for each inspected portion and/or for each inspected layer. For example, a certain type of a part may have one difficult fabrication areas prone to defects. The part-to-part comparison may be used to identify such areas and, in some embodiments, to change process parameters used for fabrication to avoid future anomalies. Furthermore, part-to-part variations may be used to identify equipment malfunctions.

In some embodiments, the method of inspecting a composite item may also involve generating a course of action for repairing the top composite layer. The course of action may be generated based on the detected anomalies on the inspected portion of the top composite layer or, more specifically, based on results of the structural integrity check. In some embodiments, the course of action may be generated based on data available from a database. This database may be referred to as an action database and may include a set of action for each detected anomaly. This course of action may be transmitted to another system, such as a user interface accessible to production personnel.

In some embodiments, the method may also involve performing the course of action and repairing the top composite layer in accordance with this course of action. For example, production personnel may receive the generated course of action and execute the operations specified in this course of action. Some examples include adding material to create an overlap between two adjacent courses that have a gap, repositioning a tow that has overlapped an adjacent tow, pressing down untacked tows that are off the surface, and/or performing other like actions. The 3D anomaly map may be updated with the repair information. In general, the 3D anomaly map may be used to store information for each anomaly and each repair previously performed on the composite item.

In some embodiments, analyzing the image also involves classifying any detected anomalies into two or more classes. For example, the detected anomalies may be classified based on type (e.g., a gap, an overlap), based on severity (e.g., low structural risk, high structural risk), or some other criteria. In a specific example, the two or more classes used for classifying may include different height variation ranges.

In some embodiments, the method also involves updating an anomaly database, such as 3D map, for the composite item based on any detected anomalies in the inspection portion. The anomaly database may keep a track of all anomalies for this part (e.g., for all composite layers and/or all inspected areas of each composite layer). The information on these anomalies may include a number of the layer containing an anomaly and a location of the anomaly within this layer. In some embodiments, the anomaly database may also keep a track of anomalies of other inspected parts. The anomaly database may also keep a track of all previous repairs performed on the part.

In some embodiments, the method also involves performing and repeating one or more of the following operations: receiving an image of another portion and/or another layer, analyzing this image, and performing the structural integrity check analysis. In some embodiments, some of these operations may be performed in batches. For example, multiple images may be received prior analyzing anyone of these images. Likewise, multiple images may be analyzed prior to performing the structural integrity check on any portions represented in these images. The 3D may be updated for each addition layer inspected and/or repaired.

In some embodiments, the method also involves applying a top composite layer over the at least one bottom composite layer and capturing an image of a portion of the top composite layer. In other words, the method of inspecting a composite item also involves production steps of applying composite layers. Overall, the method may involve an iterative loop of applying operations and inspecting operations.

In some embodiments, the method also involves receiving an additional image of an additional portion of the top composite layer. The additional portion may be adjacent to the previously inspected portion. The two portions may overlap to ensure continuity of the overall inspection. The operation of receiving additional images of different portions of the top composite layer may be repeated until the entire top composite layer is inspected. In some embodiments, a process of applying another composite layer is not started until the entire top composite layer is inspected and, more specifically, until the necessary repairs are performed. Alternatively, another composite layer may be applied over inspected (and repaired, if necessary) portions of the top composite layer while remaining portions of the top composite layer are being inspected.

The additional image of the additional portion of the top composite layer may be analyzed to detect anomalies on this additional portion. A structural integrity check may be then performed based on any detected anomalies on or more of the additional portion of the top composite layer, based on any anomalies previously detected on the underlying portion of the at least one bottom layer, and based on any detected anomalies on the portion of the top composite layer. In some embodiments, all three criteria listed above are used for the structural integrity check.

In some embodiments, receiving the image of the portion of the top composite layer involves receiving coordinates identifying location of the portion on the top composite layer. The underlying portion of the at least one bottom layer may have the coordinates. In some embodiments, the method also involves transmitting results of the structural integrity check to another computer system. For example, receiving the image, analyzing the image, and performing the structural integrity check may be performed on a computer system that is separate from production equipment used for applying the composite layer being inspected. In some embodiments, the computer system used for inspecting composite items may be in a different facility and even operated by a different entity. Once the analysis is performed, the results may be transmitted to a system used by inspection personnel and/or product personnel.

Provided also is a computer system for inspecting a composite item. The computer system may include a receiving module for receiving an image of a portion of a top composite layer. The computer system may also include a processor for analyzing the image to detect anomalies on the portion of the top composite layer and for performing a structural integrity check based on any detected anomalies on the portion of the top composite layer and based on any anomalies previously detected on the underlying portion of the at least one bottom layer.

Provided also is a computer program product including a computer usable medium having a computer readable program code embodied therein. This computer readable program code is adapted to be executed to implement a method for inspecting a composite item. The method may involve receiving an image of a portion of a top composite layer, analyzing the image to detect anomalies on the portion of the top composite layer, and performing a structural integrity check based on any detected anomalies on the portion of the top composite layer and based on any anomalies previously detected on the underlying portion of the at least one bottom layer.

These and other embodiments are described further below with reference to the figures.

DETAILED DESCRIPTION

Figure 1:
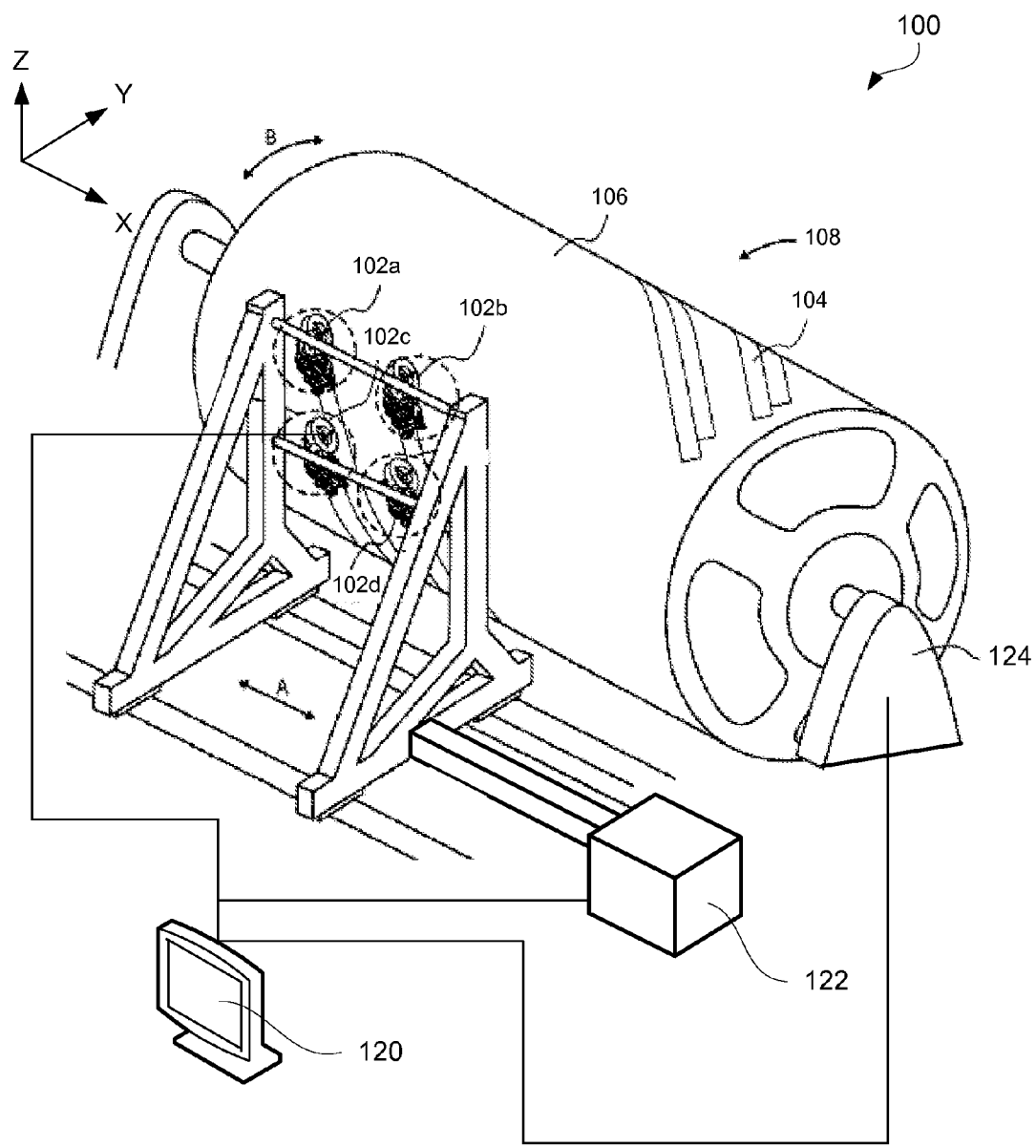
FIG. 1 is a schematic illustration of a tape lamination system, in accordance with some embodiments.

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific embodiments, it will be understood that these embodiments are not intended to be limiting.

Introduction

Composite fabrication may involve carbon fiber tape lay-down process using various lay-up machines, such as high speed lay-up machines. While these machines can apply a composite layer relatively fast, the overall process is often slowed down by inspection of the applied layer. Once applied, each composite layer is analyzed to identify, classify, and resolve various anomalies that can occur during or even after application of each layer. Inspection may be a very human intensive process and involve visually check of each composite layer. Each detected anomaly may be classified and some measures may be taken to resolve these anomalies to ensure integrity of the overall composite item.

Machine vision systems have been proposed for inspection of layers as these layers are formed. While some human induced variances have been reduced or eliminated, independent inspection of each layer fails to capture cumulative effects of anomalies in different layers. A cumulative effect may be also referred to as a stack-up effect referring to anomalies in different layers stacking up on the top of each other. Furthermore, repairs used to address anomalies in one layer generally impact repairs needed in another layer.

Provided here are methods, systems, and computer program products used to inspect composite items accounting for characteristics of multiple composite layers. Specifically, a method involves analyzing an image of a top layer disposed over a bottom layer and performing a structural integrity check based on any anomalies detected in both layers. Such process control may provide real time awareness and control for composite lay-down processes. The control may be based on in-situ inspection for composite lay-down anomalies and, in some embodiments, involve classification and rework to ensure anomaly resolution. For example, a laser scanning system may be used to sense surface distortions of a composite layer and to generate a respective image that, for example, characterizes height variations of the composite layer.

In some embodiments, the method may also involve generating a course of action in order to address the detected anomalies. For example, a decision support rule engine, which may be a policy/rule-based generator, may use results of an anomaly detection module to generate a course of action. In some embodiments, the structural integrity check further revises this course of action based on anomalies and/or repairs in other layers.

The output of a structural integrity check may include visual representations of anomaly locations, types of anomalies, and magnitude of anomalies. This output may be displayed on a computer user interface (UI) of a system used by quality control personnel and/or production personnel. This system may be also used to perform various operations of this method, such as analyzing the image to detect anomalies and/or performing a structural integrity check. In some embodiments, a system for inspecting composite items may integrated with a vision system used to capture images of composite layers and/or with a production system used to apply composite layers. Alternatively, the output may be transmitted to another system In other words, a system used for analyzing images and performing structural integrity checks may be different from the system displaying the output or, more generally, receiving the output.

Composite Fabrication Equipment Examples

Examples of systems used for applying composite layers to form composite items and for capturing images of these layers will be now briefly described to provide better understanding of various methods and systems for inspecting these composite items. In general, these methods and systems may be suitable for use with any lamination device, such as an automated fiber placement (AFP) machine, a flat tape lamination machine (FTLM), a numerically controlled (NC) contoured tape lamination machine (CTLM), a multi-head tape lamination machine (MHTLM), and the like. These lamination devices generally include at least one application head for applying a composite layer or, more specifically, for placing plies of composite material first on a mandrel and then on previously formed composite layers.

FIG. 1 is a schematic illustration of a tape lamination system 100 or, more specifically, an MHTLM system, in accordance with some embodiments. While the description below refers to the MHTLM system, it should be understood that methods for inspecting composite items described herein can be used with any lamination devices and systems. System 100 includes one or more application heads 102a-102d to apply a course 104 upon a substrate 106. While FIG. 1 illustrates system 100 with four application heads, one having ordinary skills in the art would understand that any number of application heads can be used. In general, increasing the number of heads 102a-102d increases the fabrication rate. As such, a composite item 108 may be produced in less time and/or more economically.

Applying course 104 forms a composite layer. As noted above, course 104 is applies on substrate 106. When a first composite layer is formed, substrate 106 may be a surface of a mandrel. It should be noted that performing a structural integrity check of the first composite layer may use a different procedure than performing a structural integrity check of any subsequent layer. More specifically, the first composite layer does not have any other layers disposed under the first composite layer and, as a result, the structural integrity check of the first composite layer is not based on anomalies previously detected on underlying portions of another layer. Once the first composite layer is formed on the mandrel, this first layer and then any subsequently deposited layer serves as substrate 106. A method of inspecting composite items for second and subsequent layers is performed as described below. More specifically, the method involves performing a structural integrity check based on any detected anomalies on the portion of the currently inspected composite layer and based on any anomalies previously detected on an underlying portion of the at least one bottom composite layer. Overall, by placing courses 104 on substrate 106 in this manner and forming composite layers, composite item 108 is generated.

In some embodiments, system 100 includes a controller 120 for controlling various positioning devices, such as horizontal positioning device 122 and/or a rotational positioning device 124. Horizontal positioning device 122 moves and positions application heads 102a-102d relative to substrate 106, while rotational positioning device 124 positions or rotates substrate 106 relative to application heads 102a-102d. Specifically, as shown in FIG. 1, horizontal positioning device 122 moves and positions application heads 102a-102d relative to substrate 106 along the X axis (the A direction). Rotational positioning device 124 positions or rotates substrate 106 relative to application heads 102a-102d around the X axis (the B direction). Controller 120 may also be coupled to one or more application heads 102a-102d and control operations of these heads. For example, controller 120 may change certain operation parameters of application heads 102a-102d based on the results of structural integrity check, which may be referred to as a process feedback loop. Furthermore, controller 120 may be coupled to one or more image capturing devices and control operations of these devices. In some embodiments, controller 120 may be a computer system used to perform various operations of the inspection method, such as analyzing the image to detect anomalies and performing the structural integrity check. In some embodiments, controller 120 may include a UI for presenting results of this inspection. Some aspects and examples of controller 120 are described below with reference to FIG. 3 and FIG. 7.

Each course 104 may include any suitable material to fabricate composite item 108. Examples of suitable materials include metal foils, films, fibers, and the like. These materials may be coated or impregnated with resin. In some embodiments, a course includes carbon fibers pre-impregnated with a thermoset resin, which may be referred to as a pre-preg. Course 104 may include a titanium foil coated with a resin. Composite item 108 may be any suitable item or part fabricated with course 104. Particular examples of composite items 108 include wing and fuselage components for an aircraft as further described below with reference to FIG. 6. Other examples include car and truck body and framing members and various other consumer products.

Figure 2:
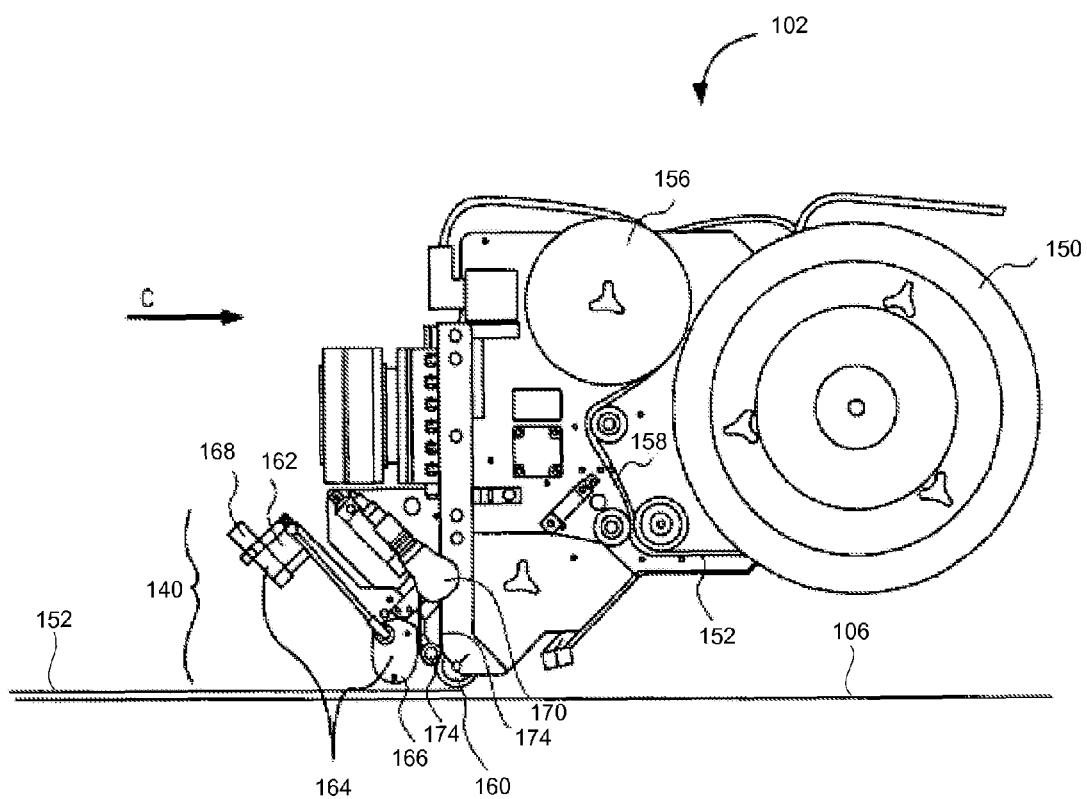
FIG. 2 is a side view of an application head suitable for use on the tape lamination system, in accordance with some embodiments.

FIG. 2 is a side view of application head 102 suitable for use on system 100, in accordance with some embodiments. Application head 102 includes a supply reel 150 to supply a tape 152 and a take-up reel 156 to retain an option backing 158 that may be removed from tape 152. Application head 102 also includes a compaction roller 160 to compact or consolidate tape 152 upon substrate 106. For simplicity, substrate 106 is shown as a flat structure in FIG. 2. However, one having ordinary skills in the art would appreciate that substrate 106 can have any shape.

Application head 102 includes vision assembly 140 for capturing an image of tape 152 after it was applied onto substrate 106 or, more generally, for capturing an image of a composite later formed by tape 152 on substrate 106. Vision assembly 140 includes sensor 162 and lighting system 164. In some embodiments, lighting system 164 includes one or more area lights 166 and laser 168. Area lights 166 are configured to illuminate an inspected area and may facilitate sensing foreign objects on tape 152. Laser 168 generates a line of illumination across tape 152 and may facilitate sensing height variations, misalignments, overlaps, gaps, and the like in course placement. Vision assembly 140 may also include an encoder 170, encoder drive 172, and belt 174 for controlling position of the inspected area, During application of tape 152 to form a composite layer, application head 102 is guided in direction "C" along the path via the various movements of the frame supporting application head 102 and movements of substrate 106 (e.g., determined by the movements of the mandrel). This movement is configured to place tape 152 upon substrate 106. Tape 152 and substrate 106 are configured to adhere to one another. For example, tape 152 and/or the substrate 106 may be tacky. Compaction roller 160 is configured to press or urge tape 152 against substrate 106 so as to consolidate tape 152 into the layup. Vision assembly 140 is configured to capture images and other characteristics of this placed tape 152.

Inspection System Examples

Figure 3:
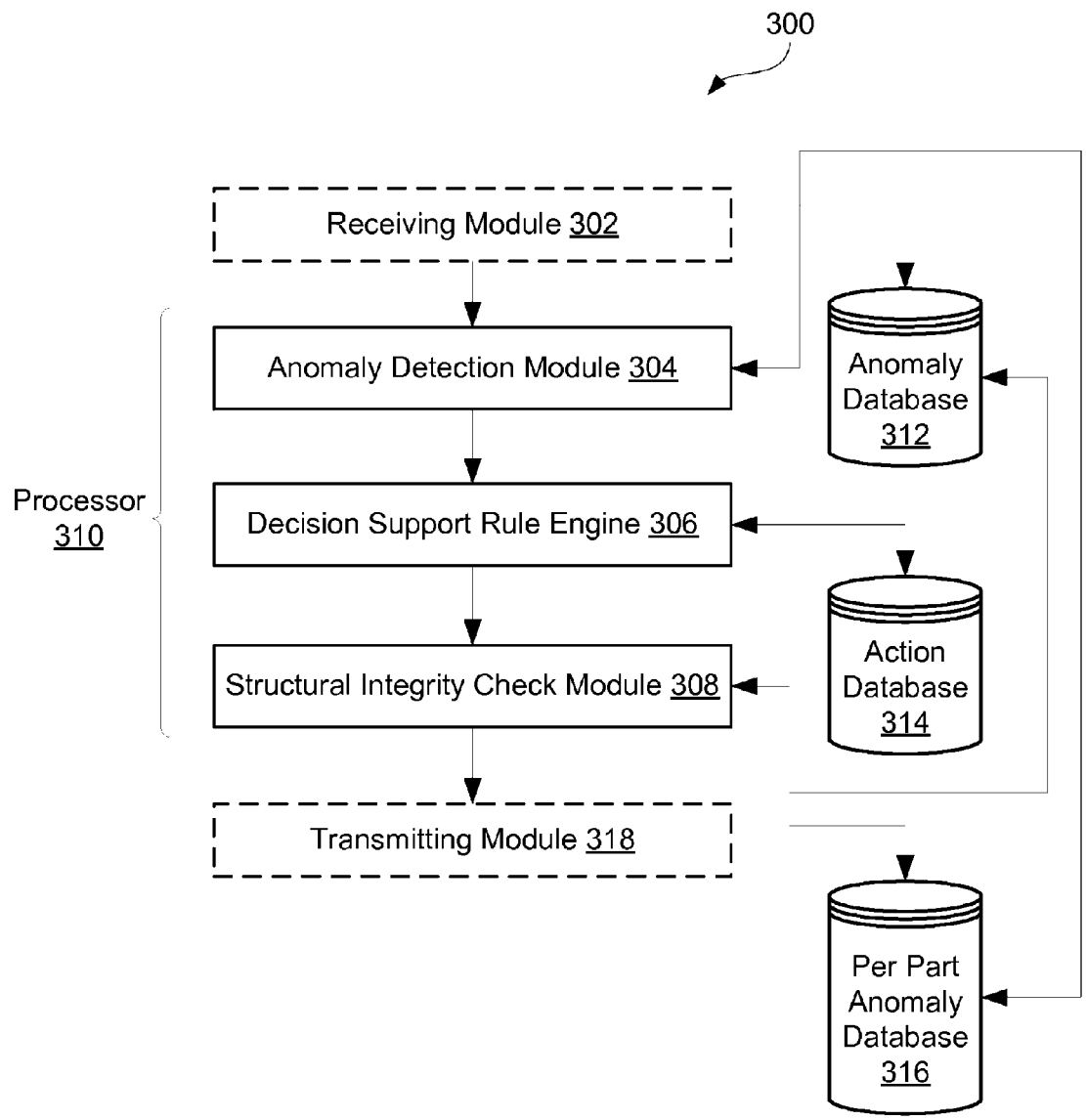
FIG. 3 is a schematic representation of a computer system for inspecting composite items, in accordance with some embodiments.

FIG. 3 is a schematic representation of a computer system 300 for inspecting composite items, in accordance with some embodiments. Computer system 300 may include an optional receiving module 302 for receiving images of composite layers, for example, from another system. Computer system 300 may also include an optional transmitting module 318 for transmitting results of a structural integrity check to, for example another system. In some embodiments, the receiving computer system may be the same system from which the images of the composite layers are sent. In some embodiments, computer system 300 may be integrated with one or more other computer systems, such as a computer system used to acquire images of composite layers, a system controller used for controlling composite laydown processes, or any other computer system. Receiving module 302 and/or transmitting module 318 may be network cards, modems, or other like communication devices.

Computer system 300 also includes a processor 310 for analyzing the received images in order to detect anomalies on composite layer presented in these images. Processor 310 may also perform structural integrity checks based on any detected anomalies on the depicted composite layers and based on any anomalies previously detected on other layers of the same part.

Processor 310 may include various modules, and it may be connected to various databases. As shown in FIG. 3, processor 310 includes anomaly detection module 304, decision support rule engine 306, and structural integrity check module 308. Processor 310 may include fewer modules than shown and/or additional modules. These modules may be in the form of hardware and/or software encoded on various hardware components, such as memory.

Anomaly detection module 304 receives images of composite layers. For purposes of this document, received images may take various forms and, in some embodiments, may be processed digital images. For example, a received image may be a photograph under areal lighting, a height variation map (e.g., generated by laser scanning), an image of a single laser line in which surface variations are indicated by changes to the straightness of the line, an image of multiple laser lines in which the surface variation is crossed more than once (providing greater fidelity of inspection) and other like images. Anomaly detection module 304 inspects the received images and detects anomalies on composite layers represented by these images. For example, anomaly detection module 304 may generate a list of all height variations that fall outside of one or more predetermined threshold ranges. The height variation may indicate the presence of an anomaly, such as a tow gap, that has a width threshold and must be measured. As a non-limiting example, a threshold might be 0.1 inches, with some repair or rework action required for anything above that. The height variation might also indicate the presence of foreign material for which there is no allowable threshold and which must be removed. These predetermined threshold ranges and/or other criteria for detecting anomalies and/or classify anomalies may be stored in anomaly database 312. Anomaly database 312 may include information on each detected anomaly. For example, a number of the layer containing an anomaly and a location of the anomaly within this layer may be captured in anomaly database 312. As such, anomaly database 312 may function as a 3D anomaly map. The detected anomalies may be classified, for example, based on their effect on structural integrity or some other factors. For example, height variations may be classified based on the level of these variations or, more specifically, which one of the height variation ranges the anomaly falls into. Anomaly detection module 304 may then send it generated results to a decision support rule engine 306. Furthermore, anomaly detection module 304 may store these results in anomaly database 312 or in per-part anomaly database 316. Per-part anomaly database 316 may be also referred to as a 3D anomaly map.

Decision support rule engine 306 receives information about detected anomalies from anomaly detection module 304 and uses this information to generate a course of action. For example, if a significant variation of height is detected, decision support rule engine 306 may generate a repair action, such as applying an additional tape at the location of this anomaly, pulling up a portion of the tape, re-laying that area with new material, and/or performing other like actions. Decision support rule engine 306 may be connected to action database 314, which stores various action options corresponding to different types of anomalies, such as repositioning a tow that has overlapped an adjacent tow and/or pressing down untacked tows that are off the surface.

Decision support rule engine 306 then sends a generated course of action to structural integrity check module 308. Structural integrity check module 308 reviews the received course of action and determines if any corrections need to be implemented in this course of action. These corrections may be based on anomalies previously detected in one or more other composite layers of this item, e.g., the composite layers disposed under the inspected layer. The information about these previously detected anomalies may be available from per-part anomaly database 316. For example, if one of the layers disposed under the inspected layer had a repair, the course of action may be change to reflect that a repair of the inspected layer may not be needed. Alternatively, if one of the layer disposed under the currently inspected layer had one or more anomalies, a more significant repair of the currently inspected layer may be needed and the course of action may be modified accordingly. Some of these aspects are further described below with reference to FIG. 4.

Inspection Methodology Examples

Figure 4:
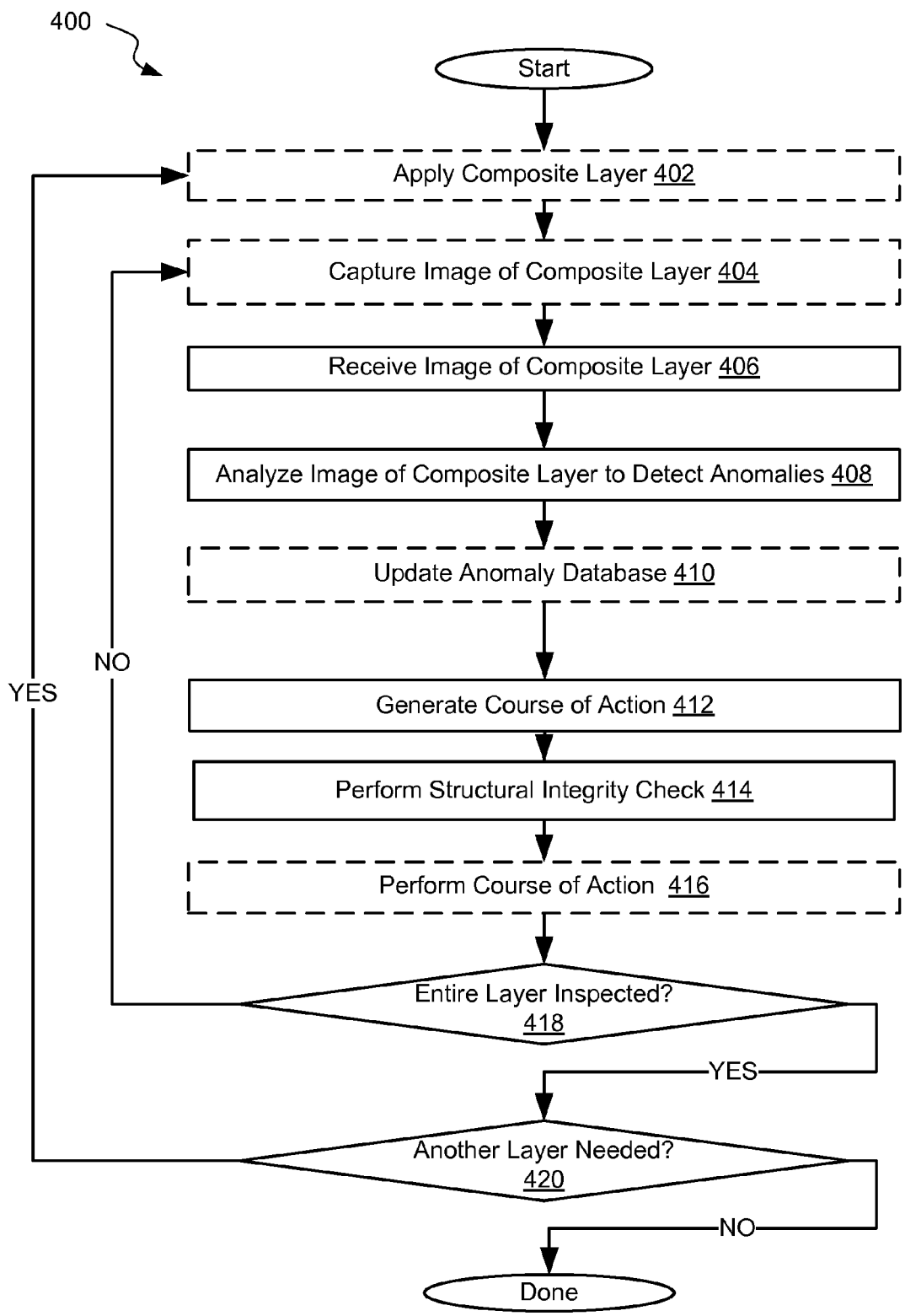
FIG. 4 is a process flowchart corresponding to a method of inspecting composite items, in accordance with some embodiments.

FIG. 4 is a process flowchart corresponding to a method 400 of inspecting composite items, in accordance with some embodiments. Method 400 may be executed by a system described above with reference to FIG. 3. Method 400 may commence with applying a composite layer during operation 402. The composite layer may be applied over another composite layer that have been previously inspected and, in some embodiments, repaired. Some aspects of applying a composite layer are described above with reference to FIG. 2.

Method 400 may proceed with capturing one or more images of the applied layer during operation 404. In some embodiments, operation 404 may involve laser scanning to determine height variations in the inspected layer. Alternatively, operation 404 may involve capturing a series of areal photographic images using a camera. These images are analyzed to determine features and variations in contrast that might indicate anomalies in the inspected layer. Furthermore, operation 404 may involve using a camera to capture images of variations in a laser line that indicate anomalies in the inspected layer.

In some embodiments, operation 404 may be performed by a device that is not a part of a system used to perform other operations of method 400, such as operations 408-416. For example, an image may be captured on a production floor by a camera that is a part of the fabrication system and is not part of the inspection system. The image may be then sent to the inspection system for performing operations 408-416.

Method 400 may proceed with receiving an image of a composite layer during operation 406. More specifically, the received image may represent a portion of the composite layer, in which case the received information may also include location coordinates of this portion on the composite layer. The received information may also include a number of the composite layer, e.g., a second layer. The image may be received by an anomaly detection module of the inspection system.

Method 400 may proceed with analyzing the received image to detect anomalies during operation 408. This operation may be performed by the anomaly detection module, which may in turn be communicatively coupled to an anomaly database as described above with reference to FIG. 3. Specifically, anomalies on the portion of the top composite layer represented in the received image are inspected for during operation 408. In some embodiments, analyzing the image involves classifying any detected anomalies into two or more classes. For examples, anomalies may be classified based on height variations of the surface of the inspected composite layer using two or more height variation ranges, each corresponding to a separate class. The structural integrity check may be then performed based on anomalies in each class. In some embodiments, anomalies in each class may have a specific coefficient (e.g., statistical weight) assigned to them based, for example, on severity of anomalies in this class. These coefficients are later used in the structural integrity check together with a number of anomalies in each class.

If any anomalies are detected during operation 408, method 400 may proceed with updating an anomaly database or a per-part anomaly database, such as a 3D anomaly map, during optional operation 410. These databases are described above with reference to FIG. 3. The anomaly database or the per-part anomaly database may include records of anomalies in previously inspected composite layers of this part and/or anomalies detected in the same layer and the same portion of other previously inspected parts. The detected anomalies may be categorized based on types of the detected anomalies, positions of the detected anomalies, identification of the inspected layer and part, performed repairs, and other like information. The anomaly database or the per-part anomaly database may be updated by the anomaly detection module. Furthermore, one or more of these database may be used to store information about repairs performed on the part.

Method 400 may proceed with generating a course of action for repairing the currently inspected composite layer during operation 412. This course of action may be generated based on the detected anomalies and may be performed by the decision support rule engine described above. In some embodiments, the decision support rule engine may select a course of actions based on data available in the action database. Specifically, the database may be searched for anomalies detected during operation 408 and retrieve course of actions corresponding to these anomalies.

Method 400 may proceed with performing a structural integrity check during operation 414. The structural integrity check may be performed based on anomalies detected during operation 408 and/or a course of action identified during operation 412. The structural integrity check is also performed based on any anomalies previously detected on the underlying portion of the at least one other layer. For example, if the captured image is of the second layer, then the structural integrity check is performed based on any detected anomalies in the second layer and any detected anomalies in the first layer. In the similar manner, if the captured image is of the third layer, then the structural integrity check is performed based on any detected anomalies in the first, second, and third layers, and so on.

In some embodiments, the structural integrity check is also performed based on any repairs performed on the underlying portion of at least one composite layer disposed underneath the currently inspected layer. The information of previously performed repairs considered during operation 414 may include types of these repairs, locations of these repairs within the portion or, more generally, the part, and the layer count corresponding to each repair. In some embodiments, the repairs may be assigned weight coefficient based on this information and some repairs may be ignored (e.g., assigned the weight of zero) because of their negligible impact on the current layer.

In some embodiments, the structural integrity check is also performed based on anomalies detected on corresponding portions of other composite items. The correspondence of these portions on the currently inspected and on the other composite items may be based on the location of portion and/or the number of the layer. This part-to-part inspection may be used to determine problems with overall fabrication and/or inspection techniques and to generate actions that not only involve repair of the currently inspected layer but also involve modification to the previously used fabrication and/or inspection techniques.

Method 400 may proceed with performing the course of action for repairing the currently inspected composite layer during operation 416. For example, the course of action may be displayed on a graphical UI accessible to production and/or inspection personnel charged with performing repairs. The course of action may indicate the location of repairs, the types of repairs (e.g., addition of material to close the gap), and any other information that be useful to the personnel. In some embodiments, operation 416 may also involve feedback from the operator about completion of the repair. This feedback may include re-inspection of the repaired area using the inspection system and prior to applying the next layer.

In some embodiments, the repairs may be performed automatically by a tape lamination system described above with reference to FIG. 1 and FIG. 2. For example, the course of action may involve change to the process recipe used for applying a subsequent composite layer (e.g., more overlaps between the courses in the subsequent layer).

Method 400 may involve repeating one or more operations 404-416 for another portion of the same layer as indicated by decision block 418. This cycle may be repeated until all portions of the layer are inspected. The subsequently inspected portion may be adjacent to the previously inspected portion. In this case, the results on the previous inspection may be considered when performing the structural integrity check on new portions. In some embodiments, one or more operations 404-414 may be repeated for the inspected portion of the composite layer after performing the course of action during operation 416. This repetition may be used, for example, to inspect one or more repairs performed during operation 416.

Method 400 may involve repeating one or more operations 404-416 for an additional composite layer disposed over the previously inspected layer composite layer as reflected by decision block 420. Specifically, once the composite layer is inspected and, in some embodiments, repaired, method 400 may proceed with applying another composite layer over that inspected layer. An image may be captured and/or received of a portion of this new layer and operations 404-416 may be repeated.

Examples of Aircrafts

Figure 5:
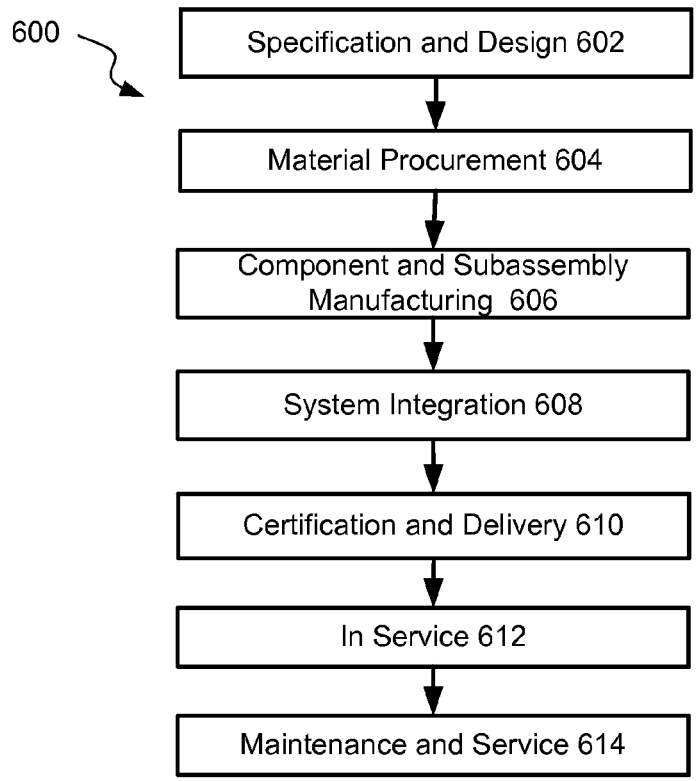
FIG. 5 is a process flowchart reflecting key operations in the life cycle of an aircraft from early stages of manufacturing (involving inspecting composite items) and to entering service, in accordance with some embodiments.

An aircraft manufacturing and service method 600 shown in FIG. 5 and an aircraft 630 shown in FIG. 6 will now be described to better illustrate various features of processes and systems for fabricating and inspecting composite items. During pre-production, aircraft manufacturing and service method 600 may include specification and design 602 of aircraft 630 and material procurement 604. The production phase involves component and subassembly manufacturing 606 and system integration 608 of aircraft 630. Fabricating and inspecting composite items may be performed during operation 606, for example. Thereafter, aircraft 630 may go through certification and delivery 610 in order to be placed in service 612. While in service by a customer, aircraft 630 is scheduled for routine maintenance and service 614 (which may also include modification, reconfiguration, refurbishment, and so on). While the embodiments described herein relate generally to servicing of commercial aircraft, they may be practiced at other stages of the aircraft manufacturing and service method 600.

Each of the processes of aircraft manufacturing and service method 600 may be performed or carried out by a system integrator, a third party, and/or an operator (e.g., a customer). For the purposes of this description, a system integrator may include, without limitation, any number of aircraft manufacturers and major-system subcontractors; a third party may include, for example, without limitation, any number of venders, subcontractors, and suppliers; and an operator may be an airline, leasing company, military entity, service organization, and so on.

Figure 6:
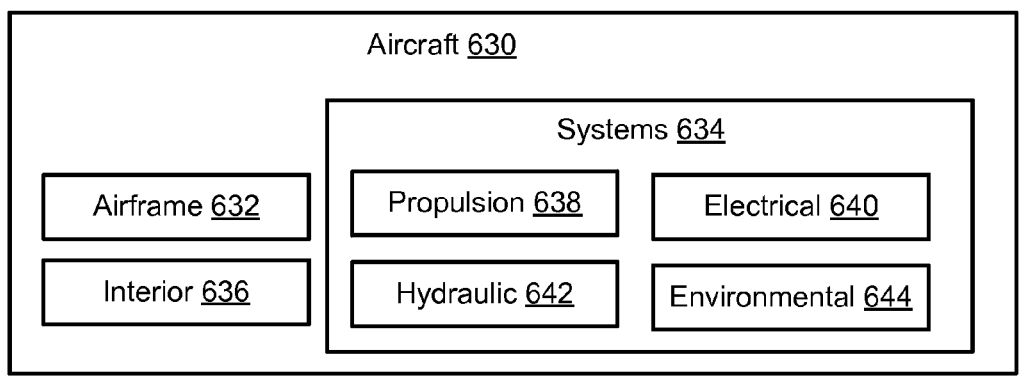
FIG. 6 is a block diagram illustrating various key components of an aircraft, some of which may include composite items, in accordance with some embodiments.

As shown in FIG. 6, aircraft 630 produced by aircraft manufacturing and service method 600 may include airframe 632, interior 636, and multiple systems 634 and interior 636. Examples of systems 634 include one or more of propulsion system 638, electrical system 640, hydraulic system 642, and environmental system 644. Any number of other systems may be included in this example. Although an aircraft example is shown, the principles of the disclosure may be applied to other industries, such as the automotive industry.

Apparatus and methods embodied herein may be employed during any one or more of the stages of aircraft manufacturing and service method 600. For example, without limitation, components or subassemblies corresponding to component and subassembly manufacturing 606 may be fabricated or manufactured in a manner similar to components or subassemblies produced while aircraft 630 is in service.

Also, one or more apparatus embodiments, method embodiments, or a combination thereof may be utilized during component and subassembly manufacturing 606 and system integration 608, for example, without limitation, by substantially expediting assembly of or reducing the cost of aircraft 630. Similarly, one or more of apparatus embodiments, method embodiments, or a combination thereof may be utilized while aircraft 630 is in service, for example, without limitation, to maintenance and service 614 may be used during system integration 608 and/or maintenance and service 614 to determine whether parts may be connected and/or mated to each other.

Examples of Controller Computer Systems

Figure 7:
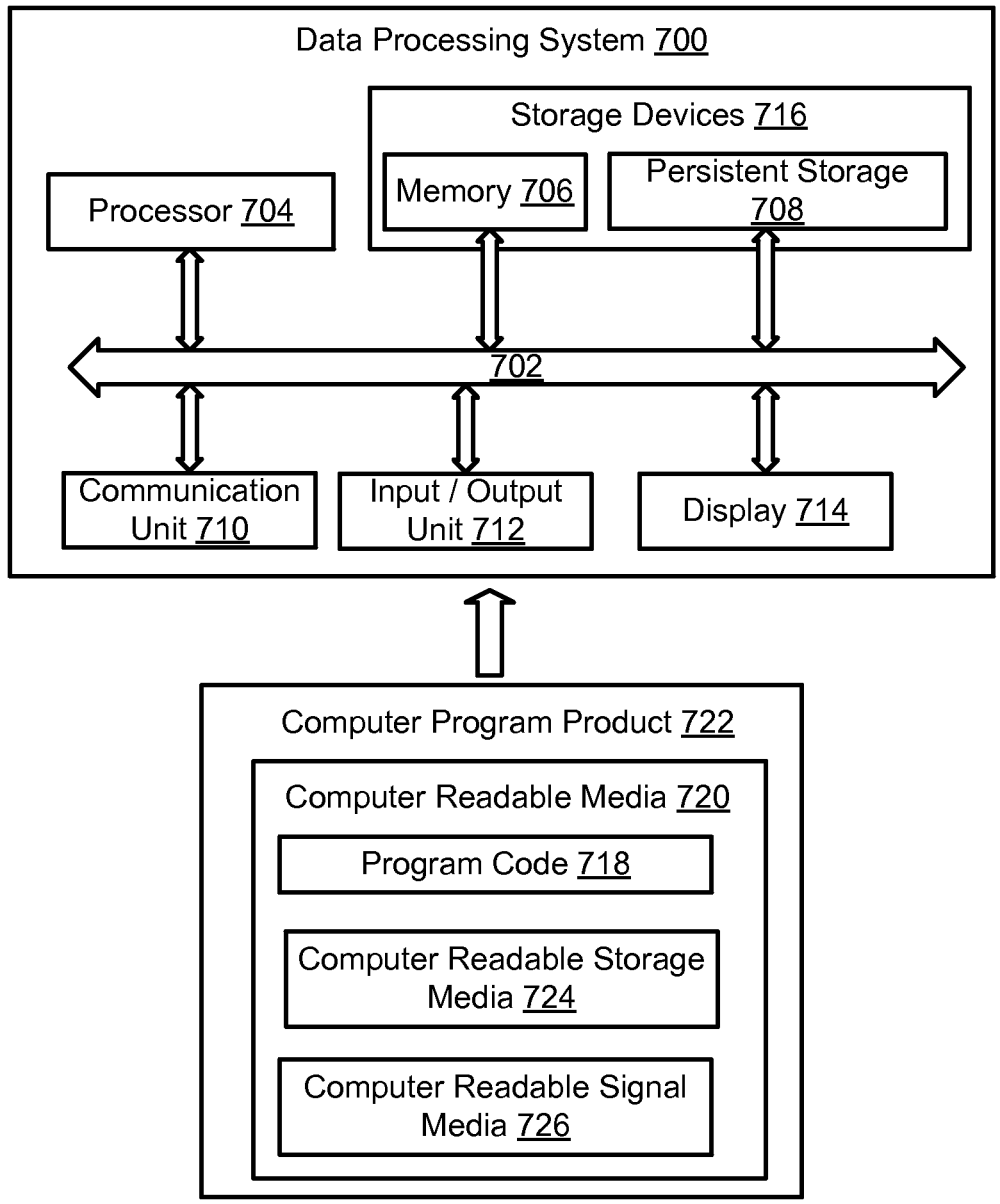
FIG. 7 is a block diagram illustrating a data processing system for inspecting composite items, in accordance with some embodiments.

Turning now to FIG. 7, an illustration of a data processing system 700 is depicted in accordance with some embodiments. Data processing system 700 may be used to implement one or more computers used in a controller or other components of various systems described above. In some embodiments, data processing system 700 includes communications framework 702, which provides communications between processor unit 704, memory 706, persistent storage 708, communications unit 710, input/output (I/O) unit 712, and display 714. In this example, communications framework 702 may take the form of a bus system.

Processor unit 704 serves to execute instructions for software that may be loaded into memory 706. Processor unit 704 may be a number of processors, a multi-processor core, or some other type of processor, depending on the particular implementation.

Memory 706 and persistent storage 708 are examples of storage devices 716. A storage device is any piece of hardware that is capable of storing information, such as, for example, without limitation, data, program code in functional form, and/or other suitable information either on a temporary basis and/or a permanent basis. Storage devices 716 may also be referred to as computer readable storage devices in these illustrative examples. Memory 706, in these examples, may be, for example, a random access memory or any other suitable volatile or non-volatile storage device. Persistent storage 708 may take various forms, depending on the particular implementation. For example, persistent storage 708 may contain one or more components or devices. For example, persistent storage 708 may be a hard drive, a flash memory, a rewritable optical disk, a rewritable magnetic tape, or some combination of the above. The media used by persistent storage 708 also may be removable. For example, a removable hard drive may be used for persistent storage 708.

Communications unit 710, in these illustrative examples, provides for communications with other data processing systems or devices. In these illustrative examples, communications unit 710 is a network interface card.

Input/output unit 712 allows for input and output of data with other devices that may be connected to data processing system 700. For example, input/output unit 712 may provide a connection for user input through a keyboard, a mouse, and/or some other suitable input device. Further, input/output unit 712 may send output to a printer. Display 714 provides a mechanism to display information to a user.

Instructions for the operating system, applications, and/or programs may be located in storage devices 716, which are in communication with processor unit 704 through communications framework 702. The processes of the different embodiments may be performed by processor unit 704 using computer-implemented instructions, which may be located in a memory, such as memory 706.

These instructions are referred to as program code, computer usable program code, or computer readable program code that may be read and executed by a processor in processor unit 704. The program code in the different embodiments may be embodied on different physical or computer readable storage media, such as memory 706 or persistent storage 708.

Program code 718 is located in a functional form on computer readable media 720 that is selectively removable and may be loaded onto or transferred to data processing system 700 for execution by processor unit 704. Program code 718 and computer readable media 720 form computer program product 722 in these illustrative examples. In one example, computer readable media 720 may be computer readable storage media 724 or computer readable signal media 726.

In these illustrative examples, computer readable storage media 724 is a physical or tangible storage device used to store program code 718 rather than a medium that propagates or transmits program code 718.

Alternatively, program code 718 may be transferred to data processing system 700 using computer readable signal media 726. Computer readable signal media 726 may be, for example, a propagated data signal containing program code 718. For example, computer readable signal media 726 may be an electromagnetic signal, an optical signal, and/or any other suitable type of signal. These signals may be transmitted over communications links, such as wireless communications links, optical fiber cable, coaxial cable, a wire, and/or any other suitable type of communications link.

The different components illustrated for data processing system 700 are not meant to provide architectural limitations to the manner in which different embodiments may be implemented. The different illustrative embodiments may be implemented in a data processing system including components in addition to and/or in place of those illustrated for data processing system 700. Other components shown in FIG. 7 can be varied from the illustrative examples shown. The different embodiments may be implemented using any hardware device or system capable of running program code 718.

Conclusion

Although the foregoing concepts have been described in some detail for purposes of clarity of understanding, it will be apparent that certain changes and modifications may be practiced within the scope of the appended claims. It should be noted that there are many alternative ways of implementing the processes, systems, and apparatuses. Accordingly, the present embodiments are to be considered as illustrative and not restrictive.

What is claimed is:

1. A method of inspecting a composite item, the method comprising:
   receiving, at a receiving module, an image of a portion of a top composite layer of a composite fabrication system, wherein the top composite layer is disposed over at least one bottom composite layer;
   analyzing the image at a detection module to detect anomalies on the portion of the top composite layer based on stored anomalies in an anomaly database; and
   generating a 3D anomaly map by integrating any detected anomalies on the portion of the top composite layer and previously detected anomalies on an underlying portion of the at least one bottom composite layer;

performing a structural integrity check at a processor based on the 3D anomaly map; and generating a course of action for repairing the top composite layer, wherein the course of action is adjusted in real-time based on the results of the structural integrity check.

2. The method of claim 1, wherein performing the structural integrity check is further based on any repairs performed on the underlying portion of at least one bottom composite layer.

3. The method of claim 1, wherein performing the structural integrity check is further based on any detected anomalies on the underlying portion of at least one bottom composite layer.

4. The method of claim 1, wherein the course of action is generated based on any detected anomalies on the portion of the top composite layer.

5. The method of claim 1, wherein analyzing the image further comprises classifying any detected anomalies into two or more classes.

6. The method of claim 5, wherein the two or more classes comprise height variations within the portion of the top composite layer.

7. The method of claim 5, wherein the structural integrity check is performed based on any detected anomalies in each of the two or more classes.

8. The method of claim 1, further comprising updating the anomaly database for the composite item based on any detected anomalies on the portion of the top composite layer.

9. The method of claim 1, further repeating receiving the image, analyzing the image, generating the 3D anomaly map, performing the structural integrity check, and generating the course of action for an additional composite layer disposed over the top composite layer.

10. The method of claim 9, further comprising applying the additional composite layer over the top composite layer while analyzing the image to detect anomalies on the portion of the top composite layer.

11. The method of claim 9, further comprising applying the additional composite layer over the top composite layer after analyzing images of all portions of the top composite layer.

12. The method of claim 1, further comprising receiving an additional image of an additional portion of the top composite layer, analyzing the additional image to detect anomalies on the additional portion of the top composite layer; and performing a structural integrity check based on any detected anomalies on the additional portion of the top composite layer, based on any anomalies previously detected on an underlying portion of the at least one bottom composite layer, and based on any detected anomalies on the portion of the top composite layer.

13. The method of claim 12, wherein the additional portion is adjacent to the portion.

14. The method of claim 1, wherein performing the structural integrity check comprises identifying severity of the detected anomaly.

15. The method of claim 1, wherein receiving the image of the portion of the top composite layer further comprises receiving coordinates identifying location of the portion on the top composite layer.

16. The method of claim 1, further comprising transmitting results of the structural integrity check to another computer system.

17. A computer system for inspecting a composite item, the computer system comprising:

a receiving module for receiving an image of a portion of a top composite layer of a composite fabrication system, wherein the top composite layer is disposed over at least one bottom composite layer;

a detection module for analyzing the image to detect anomalies in the portion of the top composite layer based on stored anomalies in an anomaly database; and a processor for:

generating a 3D anomaly map by integrating any detected anomalies on the portion of the top composite layer and previously detected anomalies on an underlying portion of the at least one bottom corn site layer, performing a structural integrity check based on the 3D anomaly map; and generating a course of action for repairing the top composite layer, wherein the course of action is adjusted in real-time based on the results of the structural integrity check.

18. A computer program product, comprising a computer usable medium having a computer readable program code embodied therein, said computer readable program code adapted to be executed to implement a method for inspecting a composite item, the method comprising:

receiving, at a receiving module, an image of a portion of a top composite layer of a composite fabrication system, wherein the top composite layer is disposed over at least one bottom composite layer;

analyzing the image at a detection module to detect anomalies on the portion of the top composite layer based on stored anomalies in an anomaly database; and generating a 3D anomaly map by integrating any detected anomalies on the portion of the top composite layer and previously detected anomalies on an underlying portion of the at least one bottom composite layer;

performing a structural integrity check at a processor based on the 3D anomaly map; and generating a course of action for repairing the top composite layer, wherein the course of action is adjusted in real-time based on the results of the structural integrity check.

* * * * *